(12) United States Patent
Gitman

(10) Patent No.: US 10,357,271 B2
(45) Date of Patent: Jul. 23, 2019

(54) SURGICAL INSTRUMENT

(71) Applicant: SCALPAL LLC, Wilmington, DE (US)

(72) Inventor: Eliot Robert Gitman, Jerusalem (IL)

(73) Assignee: SCALPAL LLC, Wilmington, DE (US)

(*) Notice: Subject to any disclaimer, the term of this patent is extended or adjusted under 35 U.S.C. 154(b) by 774 days.

(21) Appl. No.: 14/400,933

(22) PCT Filed: May 19, 2013

(86) PCT No.: PCT/IL2013/050425
§ 371 (c)(1),
(2) Date: Nov. 13, 2014

(87) PCT Pub. No.: WO2013/175463
PCT Pub. Date: Nov. 28, 2013

(65) Prior Publication Data
US 2015/0148596 A1 May 28, 2015

(30) Foreign Application Priority Data
May 20, 2012 (IL) .......................................... 219885

(51) Int. Cl.
A61B 17/32 (2006.01)
A61B 90/35 (2016.01)
(Continued)

(52) U.S. Cl.
CPC ........ *A61B 17/320016* (2013.01); *A61B 1/04* (2013.01); *A61B 17/22* (2013.01);
(Continued)

(58) Field of Classification Search
CPC ................ A61B 1/00066; A61B 1/018; A61B 2017/2925; A61B 2017/2927;
(Continued)

(56) References Cited

U.S. PATENT DOCUMENTS 4,258,716 A * 3/1981 Sutherland ..... A61B 17/320016
606/170
4,950,273 A 8/1990 Briggs
(Continued)

FOREIGN PATENT DOCUMENTS

CN 2862991 Y 1/2007
DE 29714741 10/1997
(Continued)

OTHER PUBLICATIONS

Search Report dated May 7, 2016 for Chinese Patent Application No. 201380038764 (2 pages).
(Continued)

*Primary Examiner* — Alexandra L Newton
(74) *Attorney, Agent, or Firm* — Smith, Gambrell & Russell, LLP

(57) ABSTRACT

A surgical instrument (10, 100) configured to facilitate gripping and manual adjustment by a left-handed or righted-handed user. The surgical instrument includes a rod (11) having a first end (12a) attachable to a working end (13, 113) of the instrument via a mount (16). The rod has a second end (12b) coupled to a handle (14) having rotational directionality for gripping by a first hand of the user. The handle is rotatable about the rod so as to allow the user to adjust an angular displacement of the user's finger relative to the working end, and a locking member (20, 146) prevents rotation of the handle relative to the rod when the beveled indent is optimally located relative to the working end.

29 Claims, 6 Drawing Sheets

(51) Int. Cl.
*A61B 17/3211* (2006.01)
*A61B 18/14* (2006.01)
*A61C 3/14* (2006.01)
*A61B 1/04* (2006.01)
*A61B 17/22* (2006.01)
*A61B 90/30* (2016.01)
*A61B 90/50* (2016.01)
*A61B 17/00* (2006.01)
*A61B 18/00* (2006.01)
*A61C 3/02* (2006.01)

(52) U.S. Cl.
CPC .......... *A61B 17/3211* (2013.01); *A61B 18/14* (2013.01); *A61B 18/1402* (2013.01); *A61B 90/30* (2016.02); *A61B 90/35* (2016.02); *A61B 90/50* (2016.02); *A61C 3/14* (2013.01); *A61B 2017/00424* (2013.01); *A61B 2017/00446* (2013.01); *A61B 2017/32113* (2013.01); *A61B 2018/00029* (2013.01); *A61B 2018/00035* (2013.01); *A61B 2018/00595* (2013.01); *A61B 2018/1412* (2013.01); *A61B 2090/306* (2016.02); *A61B 2217/005* (2013.01); *A61B 2217/007* (2013.01); *A61B 2218/002* (2013.01); *A61B 2218/006* (2013.01); *A61B 2218/007* (2013.01); *A61B 2218/008* (2013.01); *A61C 3/02* (2013.01)

(58) Field of Classification Search
CPC .. A61B 2017/0034; A61B 2017/00424; A61B 2017/32113; A61B 2017/2929; A61B 2017/0046; A61B 2017/0042; A61B 2017/291; A61B 17/00234; A61B 17/320016; A61B 1/00101; A61B 1/00105; A61B 17/3207; A61B 17/2909; A61B 17/3211; A61B 17/3217; A61B 17/3213; A61B 1/0052
See application file for complete search history.

(56) References Cited

U.S. PATENT DOCUMENTS

| | | | |
|---|---|---|---|
| 5,055,106 A | 10/1991 | Lundgren | |
| 5,338,292 A * | 8/1994 | Clement | A61B 10/04 604/22 |
| 5,531,754 A | 7/1996 | Shackelford, Sr. et al. | |
| 5,800,342 A * | 9/1998 | Lee | A61B 1/2676 600/114 |
| 6,142,931 A * | 11/2000 | Kaji | A61B 1/31 600/102 |
| 6,482,219 B1 | 11/2002 | Bonnet | |
| 6,517,539 B1 * | 2/2003 | Smith | A61B 17/32056 606/113 |
| 7,101,382 B2 | 9/2006 | George et al. | |
| 7,150,754 B2 | 12/2006 | Ziemer | |
| 8,506,578 B2 | 8/2013 | Smith | |
| 8,850,662 B2 | 10/2014 | Gitman et al. | |
| D731,057 S | 6/2015 | Gitman | |
| D746,460 S | 12/2015 | Gitman | |
| D755,338 S | 5/2016 | Slank | |
| D755,969 S | 5/2016 | Gitman | |
| 9,717,521 B2 | 8/2017 | Gitman | |
| 2004/0054377 A1 * | 3/2004 | Foster | A61B 10/04 606/167 |
| 2005/0267502 A1 | 12/2005 | Hochman | |
| 2007/0162095 A1 * | 7/2007 | Kimmel | A61B 1/00089 600/109 |
| 2009/0287236 A1 * | 11/2009 | Bakos | A61B 1/018 606/180 |
| 2010/0005630 A1 | 1/2010 | Gitman et al. | |
| 2010/0095969 A1 * | 4/2010 | Schwartz | A61M 25/0136 128/207.14 |
| 2011/0087255 A1 * | 4/2011 | McCormack | A61B 5/04005 606/167 |
| 2012/0029542 A1 * | 2/2012 | Huang | A61B 17/320036 606/167 |
| 2012/0071857 A1 * | 3/2012 | Goldfarb | A61B 17/24 604/514 |

FOREIGN PATENT DOCUMENTS

| | | |
|---|---|---|
| EP | 2415403 | 2/2012 |
| GB | 2271738 | 4/1994 |
| GB | 2342611 A | 4/2000 |
| WO | 0110321 | 2/2001 |
| WO | 02087420 | 11/2002 |
| WO | 2004021865 | 3/2004 |
| WO | 2015/118521 A1 | 8/2015 |

OTHER PUBLICATIONS

Office Action dated May 30, 2016 for Chinese Patent Application No. 201380038764 (3 pages in Chinese with English Translation).
International Preliminary Report on Patentability dated Nov. 25, 2014 in for International Patent Application No. PCT/IL2013/050425 (10 pages).
Communication from the Examining Division dated Nov. 2, 2016 for European Patent Application No. 13734516.1 (5 pages).

* cited by examiner

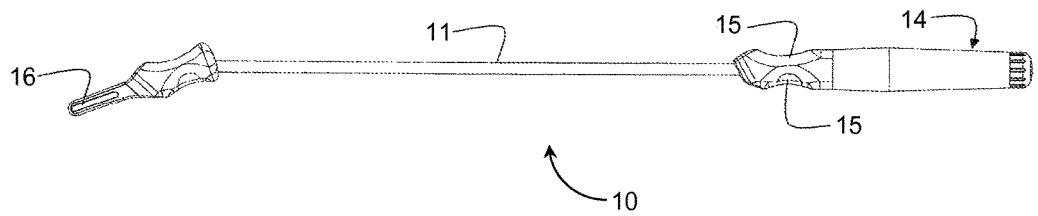
FIG. 1a
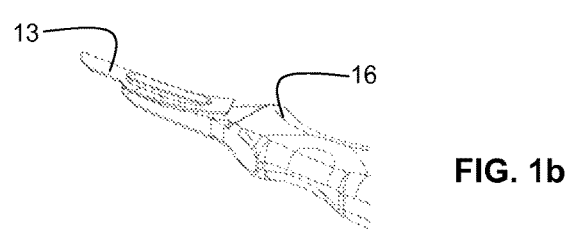
FIG. 1b
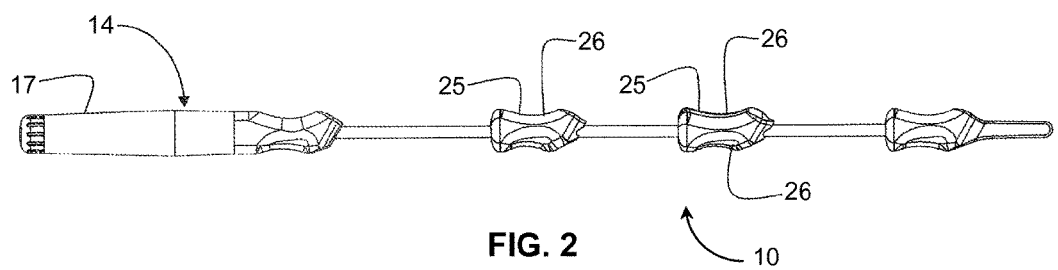
FIG. 2
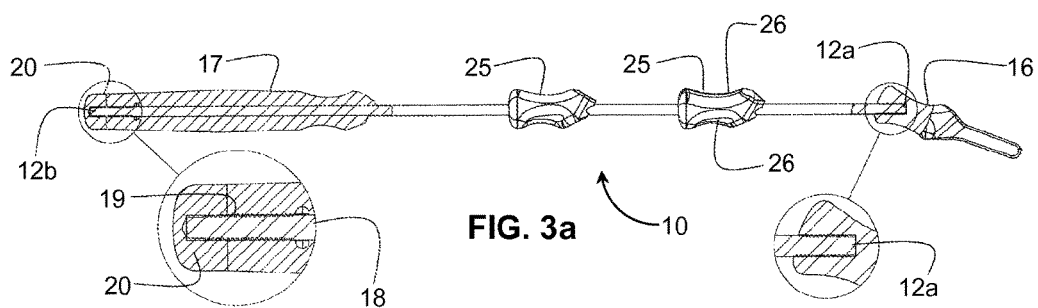
FIG. 3a
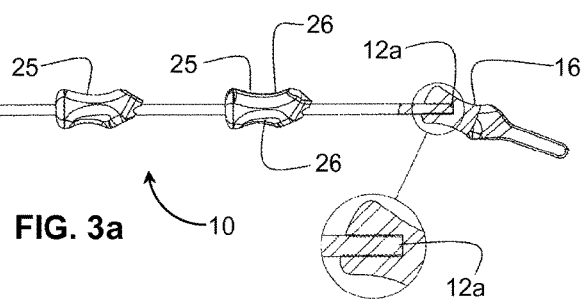
FIG. 3c
FIG. 3b

SURGICAL INSTRUMENT

FIELD OF THE INVENTION

The present invention relates to surgical instruments, particularly but not limited to surgical scalpels.

BACKGROUND OF THE INVENTION

Standard scalpel handles with flat gripping arrangements do not provide contoured gripping surfaces to keep the index finger, thumb and middle finger in place. Moreover, standard scalpel handles with flat body handle gripping arrangements can lead to slippage of the fingers onto the blade or an uncontrolled rolling between the fingers.

Many innovative scalpel handle designs have been implemented in order to address issues related to ergonomic requirements of a scalpel grip. Some of these address the protection of the scalpel user from the danger of the sharp blade, examples being U.S. Pat. Nos. 5,531,754 and 7,101,382.

U.S. Pat. No. 7,150,754 to Ziemer is directed to the alignment of a scalpel blade without the necessity for eye contact. To this end, there is provided a handle region comprising three lateral faces, which are disposed such that a cross section with a triangular envelope results for the handle region, and at least one of the lateral faces is provided with tactile identifying features. The triangular envelope of the cross section of the handle region facilitates a proper holding of the scalpel blade holder between middle finger, thumb and index finger, the scalpel blade holder and thus the scalpel fixed thereto being able to assume only three different rotational states about the center axis of the handle region of the scalpel blade holder, with respect to the fingers. The limitation in movement to only three rotational states allows the user to determine the alignment of the scalpel blade holder and of the scalpel affixed thereto via his fingers by means of his sense of touch.

U.S. Pat. No. 5,055,106 discloses a scalpel comprising a shank having a holder for releasably mounting a surgical blade. The holder includes a sleeve, which is threadedly engaged with the shank at one end thereof and adapted to be screwed axially along the shank. The sleeve forms a ball socket, which is adapted to receive therein a ball fixed to the blade.

U.S. Pat. No. 6,482,219 discloses a stricture scalpel for endoscopic use having a blade with a cutter and a stem which is inserted into the distal end of a shank.

US 20050267502 discloses a safety scalpel having a tubular housing, a coupling reciprocating within the housing and holding a cutting head or blade and a control member used to selectively extend the cutting head outwardly of the housing and retracted into the housing. A tubular groove on an inner surface of the housing may be used to simultaneously translate the cutting head and rotate it about a longitudinal axis of the housing. The cutting head can be immobilized within the housing by jamming the control tab or by removing the control tab from the housing.

Flat or triangular shaped devices are not comfortable for the user, as these handles do not sufficiently cater to the ergonomic requirements of a grip. Flat body handles provide textured gripping surfaces for the fingers, but are too small or too narrow to grip comfortably for extended periods of time, or once gripped restrict the free movement of the hand. Furthermore, flat body handle gripping arrangements can only be used basically in one position without the danger of slippage or rolling between the fingers accompanied by the risk of consequent injury to the user or the patient. Grips having triangular cross-sections may present an ease of orientation positioning, however, they fall short of providing ergonomically comfortable working solutions. One edge of the triangular shaped device can dig into a user's finger.

US 2010-0005630 in the name of the present Applicant discloses an ergonomic handle for surgical tools designed to facilitate the positioning of the user's hand grip and comprising a longitudinally extending body substantially oval in cross-section and being provided with four, substantially concave indentations positioned towards the proximal end of the handle, a first concave indentation being provided along a top surface of the handle, second and third indentations being provided along lateral surfaces, and a fourth indentation being provided along the bottom surface of the body respectively and positioned relative to each other to provide a contiguous interface respectively with the user's thumb, index finger and middle finger.

Known scalpels, including those configured for deep surgery, suffer from a number of drawbacks. First, they are not equally suited for use by left- and right-handed users since the finger grip is axially fixed relative to the blade. Consequently, an indent that is well adjusted for a right-handed user will not be comfortable for use by a left-handed user and vice versa. Secondly, they do not address the need to minimize the fatigue caused by the need to adjust relative position of fingers and maintain an assured operational control and alignment of the scalpel blade during surgery.

Yet a further consideration associated with surgical scalpels and other surgical instruments is the need for very fine adjustment during surgery. Thus, there is often a need to move the blade of a scalpel forward or sideways by a very small controlled amount. This requires extremely fine balance and places severe strain on the wrists of the surgeon.

SUMMARY OF THE INVENTION

Therefore an object of the present invention is to alleviate the drawbacks of prior art scalpels and to provide a scalpel that allows better linear and rotational control during use and is comfortable for left- and righted-handed surgeons.

To this end there is provided in accordance with one aspect of the present invention a surgical instrument configured to facilitate gripping and manual adjustment by a left-handed or righted-handed user, said surgical instrument comprising:

a rod having first and second ends, the first end fixedly attachable to a working end of the instrument and the second end coupled to a handle having rotational directionality for gripping by a first hand of the user, the handle being rotatable about the rod so as to allow the user to adjust an angular displacement of said finger relative to the working end, and a locking member for preventing rotation of the handle relative to the rod when the beveled indent is comfortably located relative to the working end.

In accordance with another aspect of the invention, there is provided a surgical instrument configured to facilitate gripping and manual adjustment by a left-handed or righted-handed user, said surgical instrument comprising:

a rod having first and second ends, the first end attachable to a working end of the instrument via a mount and the second end being adapted for gripping by a first hand of the user, and a sliding sleeve mounted on the rod intermediate the first and second ends and having a beveled indent for accommodating a user's finger of a second hand of the user.

By making the rod sufficiently long, such a surgical instrument may be suitable for deep surgery. In practical embodiments, the rod may have a range of lengths depending on the use of the surgical instrument. Thus, small rods may have a diameter of 2.5 mm and a length of 4.5 cm; medium rods may have a diameter of 4 mm and a length of 25 cm and rods for deep surgery may have a diameter of between 4-12 mm and a length in excess of 60 cm. These dimensions are of course representative and are not intended to be limiting. In order to improve structural rigidity, the rod particularly when used for deep surgery may have a stepped cross-section and is preferably formed of stainless steel.

In some embodiments of the invention, there may further be provided at least one sliding sleeve mounted on the rod and having a beveled indent for accommodating a user's finger of a second hand of the user.

The handle has rotational directionality in the sense that it may be rotated for optimal comfort or effectiveness when gripped by a hand of the user, be it the left or right hand depending on whether the user is left- or right-handed. This ensures that when the user holds the handle comfortably, the working end of the instrument may be properly oriented for optimal effectiveness. To this end, the handle may be an ergonomic handle wherein the surface area of the top of the handle is contoured such that extending from its distal end toward its proximal end and approaching the proximal end there is provided a concave indentation which extends and merges into an elevated ridge-like surface support which tapers angularly towards the proximal end of the handle. Such a handle is described in above-mentioned US 2010-0005630. Moreover, rather than employing a textured grip known for the softness or porosity thereof making sterilization difficult, the handle may be manufactured from non-textured materials, thereby creating a formed grip which is easy to sterilize.

In accordance with another aspect, the invention provides a tool rest that may be mounted transverse of a patient during surgery and used to support the surgical instrument, serving as a fulcrum allowing the surgical instrument to be pivoted and manipulated. The tool rest may be a cylindrical bar having circumferential grooves of varying widths for supporting the tool handle therein and allowing it to be tilted both up and down as well as sideways. The bar may have a diameter that is the same as that of the concave indentation in the handle, thus allowing the handle to be supported by the tool rest. In those embodiments where one or more sliding sleeves are mounted on the rod, the diameter of the rod may be the same as that of the beveled indent, so as to support the sliding sleeve.

BRIEF DESCRIPTION OF THE DRAWINGS

In order to understand the invention and to see how it may be carried out in practice, embodiments will now be described, by way of non-limiting example only, with reference to the accompanying drawings, in which:

FIGS. 1a and 2 are pictorial representations of a surgical scalpel according to different embodiments of the invention;

FIG. 1b shows pictorially a detail of the scalpel depicted in FIGS. 1a and 2;

FIG. 3a is a partial cross-section of the surgical scalpel shown in FIG. 2;

FIGS. 3b and 3c show in enlarged cross-section details of the surgical scalpel shown in FIG. 2;

DETAILED DESCRIPTION OF EMBODIMENTS

Figure 4A:
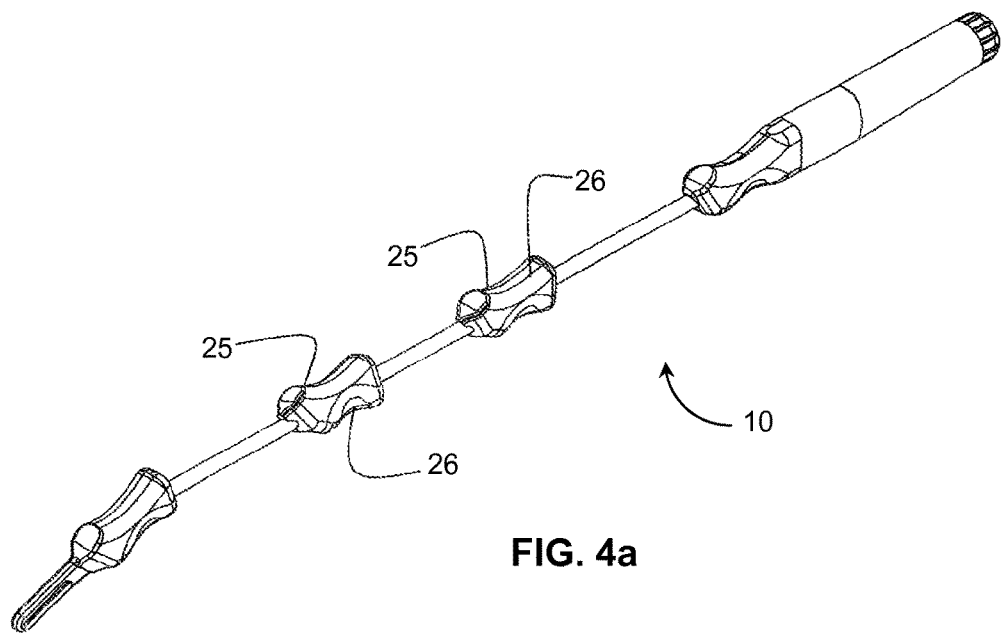
FIGS. 4a and 4b are perspective views showing surgical scalpels having working tips adapted for orientation in different directions.

In the following description of some embodiments, identical components that appear in more than one figure or that share similar functionality will be referenced by identical reference symbols.

Referring to the figures, there is shown a surgical scalpel 10 (constituting a surgical instrument) comprising a rod 11 having a first end 12a and a second end 12b. The first end 12a is fixedly attachable to a blade 13 constituting a working end of the scalpel and the second end 12b is coupled to a handle 14 having one or more beveled indents 15 for accommodating a finger of a first hand of a user. Such a handle has rotational directionality in the sense that it may be rotated for optimal comfort when gripped by a hand of the user, be it the left or right hand depending on whether the user is left- or right-handed. As shown in FIG. 1b, the blade 13 is fixedly supported in a mount 16 formed of a metal casting or plastic molding formed, for example, from polyphenylsulfone (PPSU) and having an end that is internally screw-threaded for engaging a complementary external screw thread on the rod, whereby the blade may be fixedly attached to the rod. The mount 16 may likewise having one or more concave indents for allowing the user to grip it between thumb and index finger or to support the blade with a finger, thereby facilitating precise support and adjustment during use. The mount 16 may be attached to the rod in other ways, for example by welding, gluing, crimping and so on. Likewise, the tool need not be a blade and the invention contemplates other working ends, such as probes, needles, lighting fixtures, mirrors, temperature and pressure devices, and so on. The working end can also be a cauterizing head; it may be a cannula, an electrical or air-propelled motor. The indents allow for a closer anchoring of the user's pinky finger as a support for greater precision work. The closer the user's grip is to the front of the handle for close up work the easier it is to use the instrument effectively.

As shown in FIG. 3c, the handle 14 has a generally cylindrical body 17 having an axial bore 18 that is dimensioned to accommodate the rod and an end of which has an internal screw thread 19 that is complementary to an external screw-thread on the end of the rod. The rod 11 is inserted into the axial bore 18 of the handle until it reaches the internal screw thread. The handle 14 is then screwed on to the rod 11 until a portion of the rod protrudes through the open end of the handle. Once the screw threads of the handle and the rod are thus engaged, turning the handle induces rotation of the beveled indents 15, thereby allowing the handle to be aligned with a desired direction of the blade without the need for the user to twist his or her wrist. A locking member 20 in the form of a cap has an internally threaded bore complementary to the screw thread of the small portion of the rod 11 protruding through the end of the handle 14. The cap is tightened on to the protruding rod until it frictionally bears on the end of the handle thereby preventing further rotation of the handle relative to the rod. The rod may be of circular cross-section. Alternatively, it may be of non-circular cross-section in order to prevent rotational displacement of the rod relative to the beveled indents 15.

In alternative embodiments, the locking member may include a collet inside the handle that accommodates the rod, and to which radial pressure may be applied by a radial locking screw so as to secure the handle on to the rod.

In some embodiments, the handle 14 has four concave molded indentations 15 adjoining the proximal end of the handle 14. Two of the indentations are designed to accommodate the middle finger and the thumb, respectively, while the other two indentations are designed to generally accommodate the index finger and the middle finger respectively, thereby facilitating gripping by a user. Thus, the user fingers are free from being confined to the grip positions of the handle when in use. The general configuration of the indentation according to the embodiment of the invention allows for the user to comfortably grip the handle 14 in various gripping positions. When the blade is moved from side to side, it may be more comfortable for the surgeon to rotate the handle axially relative to the blade. As noted above, this is facilitated by the manner in which the handle is attached to the rod.

Figure 4B:
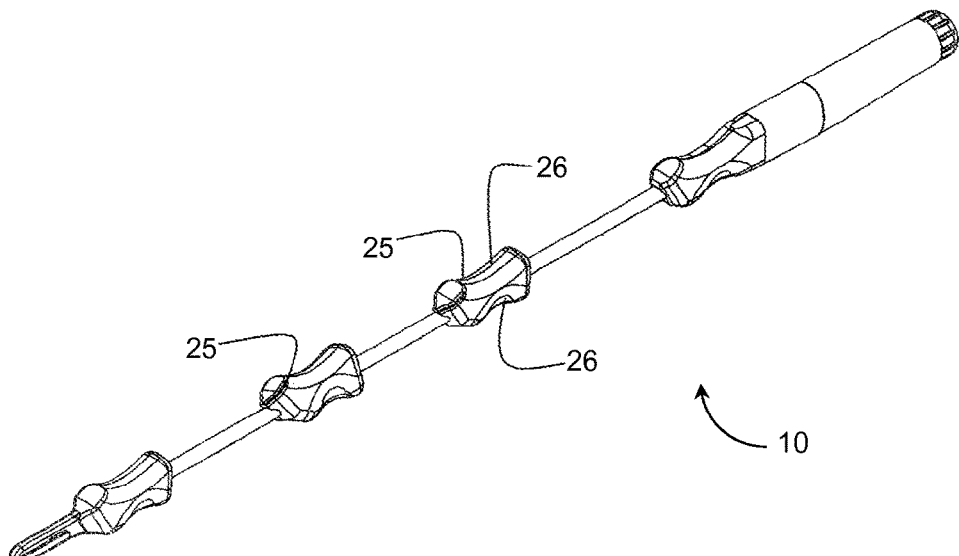

As shown in FIGS. 2 to 4, there may optionally be provided at least one sliding sleeve 25 mounted on the rod 11 and having a beveled indent 26 for accommodating a user's finger of a second hand of the user. In the case that two such sleeves are provided as shown in FIG. 2 for example, one is dimensioned for fairly freely sliding along the rod while the other is dimensioned for frictionally gripping the rod, while allowing it to be moved when desired. By such means, one of the sliding sleeve 25 is gripped by the user's second hand allowing the scalpel to be adjusted using his or her first hand. The other sliding sleeve may serve as a safety stop that prevents the blade from over-shooting.

In accordance with another aspect, the invention provides a tool rest that may be mounted transverse of a patient during surgery and used to support the tool, serving as a fulcrum allowing the tool to be pivoted and manipulated. The tool rest may be a cylindrical bar having circumferential grooves of varying widths for supporting the tool handle or the rod therein and allowing it to be tilted both up and down as well as sideways. The bar may have a diameter that is the same as that of the concave indentation in the handle, thus allowing the handle to be supported by the tool rest. In those embodiments where one or more sliding sleeves are mounted on the rod, the diameter of the rod may be the same as that of the beveled indent, so as to support the sliding sleeve. The tool rest may be supported on a retractor that is used by a surgeon either to separate the edges of a surgical incision or wound, or to hold back underlying organs and tissues, so that body parts under the incision may be accessed. This allows very close proximity to the body tissues being cut, thus allowing the surgeon close access and improved control with reduced physical strain. It should be noted that the bar need not be uniformly circular in cross-section. For example it may be generally of square cross-section with arcuate islands of generally complementary shape to the contours of the beveled indents.

In the embodiments so far described, the handle is a crucial feature of the instruments, which are configured for gripping in one hand of the surgeon while the working end of the instrument is manipulated with the other hand. However, there may be instances when the surgical instrument is manipulated not by the handle but rather by a sliding sleeve such that the surgeon grips the sliding sleeve with one hand and operates the working end with the other hand. While typically a handle is provided it is not used when operating the tool and rotational directionality is therefore not required. A surgical instrument according to such an embodiment thus comprises a rod having first and second ends, the first end attachable to a working end of the instrument and the second end being adapted for gripping by a first hand of the user, and a sliding sleeve mounted on the rod intermediate the first and second ends and having a beveled indent for accommodating a user's finger of a second hand of the user.

Therefore in the following description of various embodiments, it is to be understood that where the instrument is operated via the working end and a sleeve intermediate the handle and the working end, the handle may or may not have rotational directionality and could, indeed, even conceivably be omitted altogether.

Figure 5:
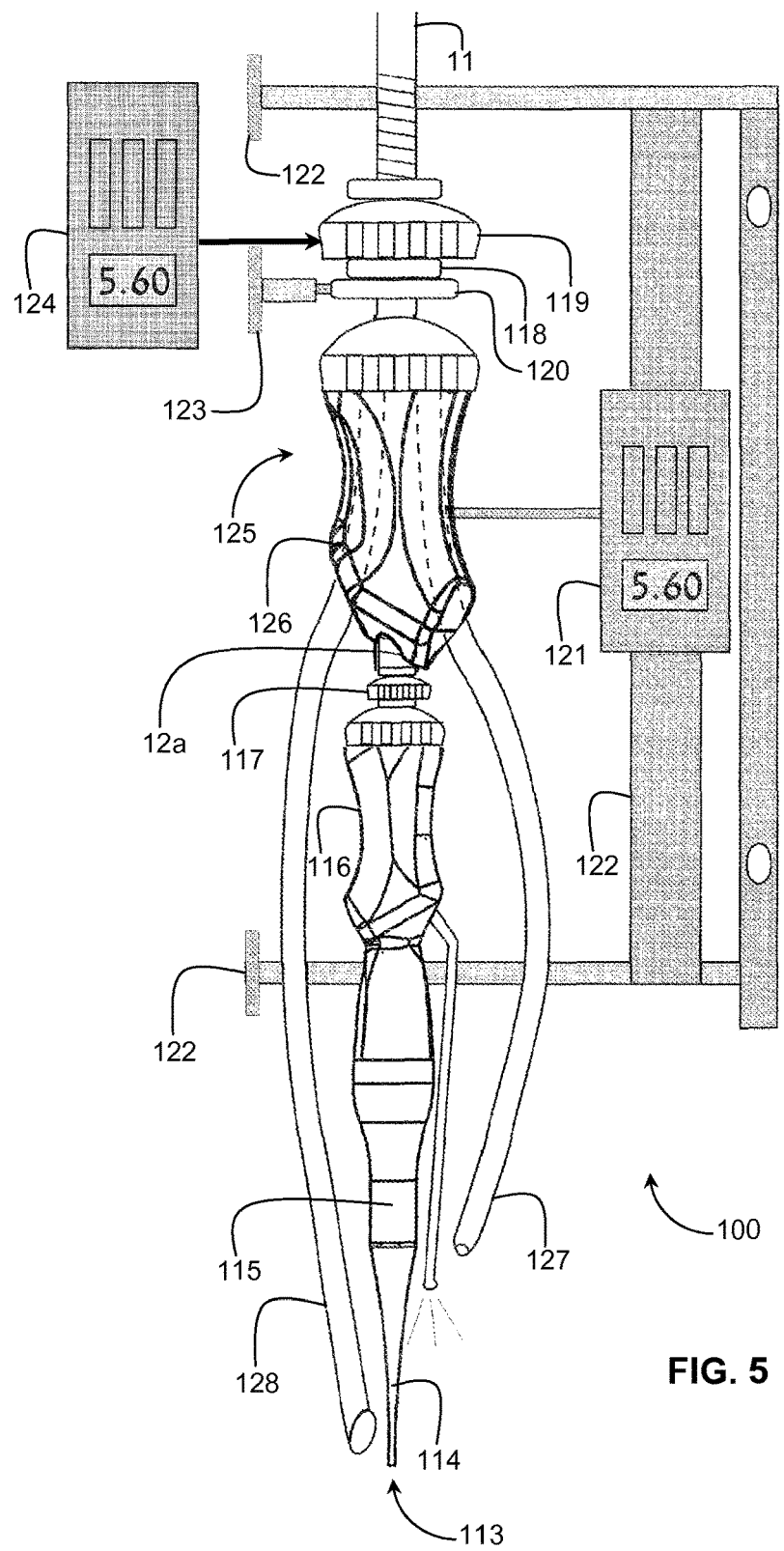
FIG. 5 is a pictorial representation showing a precision surgical instrument having optional features according to other embodiments of the invention.

FIG. 5 shows pictorially a precision surgical instrument 100 having optional features according to other embodiments of the invention. By way of illustration, a rod 11 supports at its first end 12*a* a working end 113 of the surgical instrument and at an opposite end supports a handle (not shown). The handle may be identical to the handle 14 as described above with reference to FIGS. 1 to 4. Alternatively, the handle may lack rotational directionality. The surgical instrument 100 is shown as a probe, which could be a cutting tool or cauterizing head having electrical elements, and so on. It could also be a drill such as used in dental or bone surgery, or a hooking element for extracting tissue or other artifacts from a patient. In the case that the working end 113 is a drill, the tip 114 may be the rotating barrel or chuck of the drill and a rear portion 115 may be shaped for comfortable gripping by the user. In some embodiments, the working end 113 may be fixed to a beveled mount 116 that is shaped and dimensioned to allow the working end to be gripped near to its end and to be rotated without fouling the working end. The beveled mount 116 is fixed at the first end 12*a* of the rod 11. In some embodiments, the beveled mount 116 is fixedly anchored at the end of the rod 11. However, as shown schematically in FIG. 5, it may also be capable of sliding movement to allow the working end 113 to be protracted and retracted. To this end, the mount 116 may include a self-locking collar that slides on the end of the rod and has a quick finger release that is depressed to allowing sliding and is released to lock the mount in place. Alternatively, a locking nut 117 may be provided to secure the mount 116 and prevent further sliding.

In some embodiments the first end of the rod 11 is adapted for to and fro micro-movement. This may be accomplished by a threaded bearing shown schematically as 118 that is rotatable by a knurled wheel 119 within a sleeve 120 that is fixedly anchored in space. Turning the wheel 119 rotates the threaded bearing 118 thereby inducing linear motion of the rod 11 in a direction that depends on the direction of rotation of the knurled wheel 119. If desired, a digital caliper 121 may be attached to the mount 116 or to an accessory mounted thereon so as to measure the extent of linear movement of the rod 11. The digital caliper 121 rides along a bar 122 anchored in space. In the figure, the anchors are represented by blocks 123 which are directly or indirectly fixed to ground. The knurled wheel 119 may be responsively coupled to a controller 124 so as to allow a desired linear displacement of the rod to be set. The controller is adapted to turn the knurled wheel 119 through the appropriate angular displacement to effect the required linear movement based on the known pitch of the thread.

Also shown in FIG. 5 is an accessory 125 that is mounted on the rod 11 toward the working end 113. The accessory 125 includes a mount 126 that may be fixedly or slidably mounted on the rod and supports at least one ancillary tool that is used in conjunction with the working end 113 so as to facilitate the surgical procedure being carried out without the need for auxiliary staff to hold and operate the accessory 125.

Figure 6:
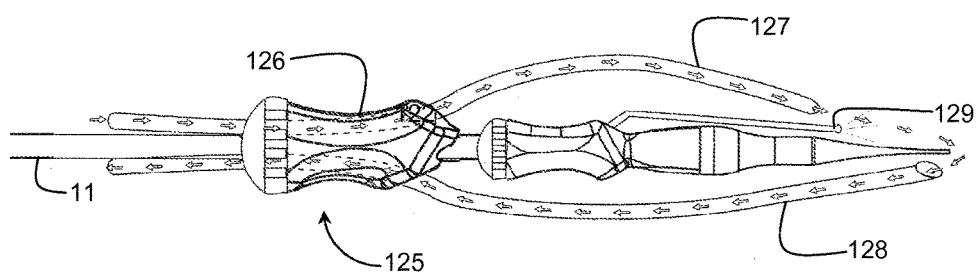
FIG. 6 is a pictorial representation showing a detail of an optional accessory that may be mounted in association with the surgical instrument shown in FIG. 5.

FIG. 6 shows a detail of the accessory 125 adapted for use with a cauterization tip or drill used as the working end 113 and which includes first and second tubes 127 and 128 that are supported within the mount 126 for conveying a fluid (i.e. gas or liquid) to or from the working end. Preferably, the mount 126 is a self-locking collar that slides on the end of the rod and has a quick finger release that is depressed to allowing sliding and is released to lock the mount in place. This allows the accessory 125 to be moved relative to the working end 113 as described below with reference to FIGS. 7a, 7b, 8a and 8b. The first tube 127 is coupled to a source of air or cutting fluid such as water that directs a jet or mist of air or water toward the working end 113, either for cooling the working end or removing debris or smoke. The second tube 128 is coupled to a vacuum source for removing smoke, debris and liquid thereby maintaining a clear field of view to the surgeon. The tubes 127, 128 may be formed of medical silicone or any other suitable material. An illumination device 129 may also be fixed to the mount 116 of the working end 113 to direct light to the field of view. In some embodiments, the mount 116 is rotatable on the rod 11, thus allowing the illumination device 129 to be rotated independent of the accessory 125. Alternatively, the illumination device 129 may be mounted on the mount 126 of the accessory 125.

Figure 7A:
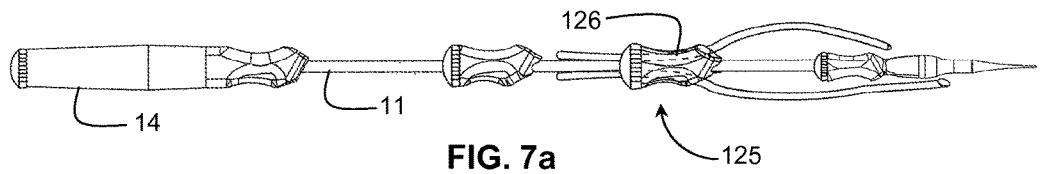
FIGS. 7a and 7b show schematically movement of the accessory relative to the working end of the tool.
Figure 7B:
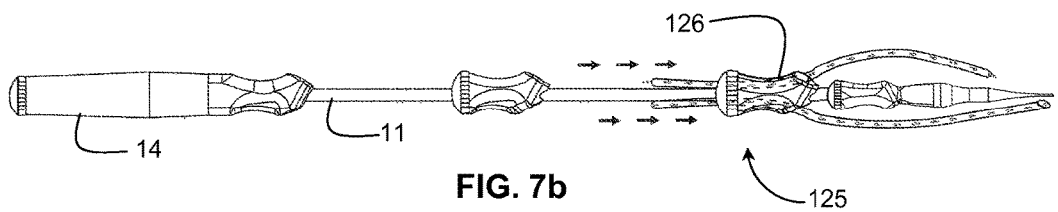

FIG. 7a shows an initial position where the accessory 125 is retracted prior to use. FIG. 7b depicts forward movement of the accessory 125 to an operational position corresponding to the situation shown in FIG. 6 and described in detail above.

Figure 8A:
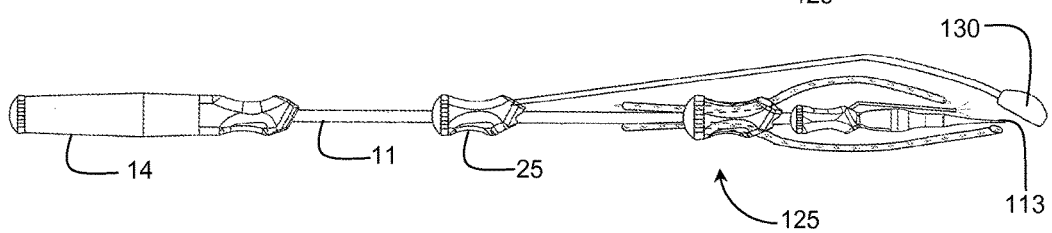
FIGS. 8a and 8b are pictorial representations showing further embodiments of an ancillary tool mounted in a sliding sleeve.

FIG. 8a is a pictorial representation showing a further embodiment where an ancillary tool 130 is mounted in the sliding sleeve 25 and adapted for sliding movement relative to the working end 113. The sliding sleeve 25 may be a self-locking collar that slides on the end of the rod and has a quick finger release that is depressed to allowing sliding and is released to lock the mount in place. The ancillary tool 130 may be a mirror, a rear surface of which may also be used as a shield for displacing material so as to allow unimpeded access to the working end 113. Alternatively the ancillary tool 130 may be an imaging device that may be coupled to a display device so as to permit the surgeon to see the field of view. In some embodiments, more than one ancillary tool may be mounted on the sliding sleeve 25.

Figure 8B:
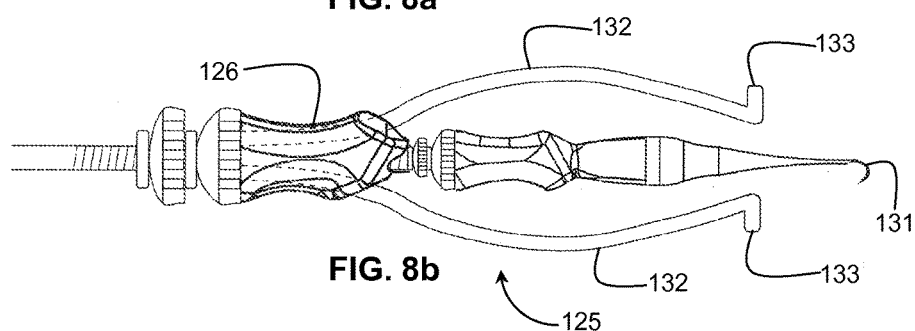

FIG. 8b is a pictorial representation showing yet another embodiment of an accessory 125 configured as a bracing element for sliding movement relative to an extraction tool 131 depicted by a hook and constituting the working end of the surgical instrument. The extraction tool 131 is adapted to extract body tissue, for example a tooth. The bracing element has a pair of opposing legs 132 fixed to a mount 126 and terminating in feet 133. When used to extract a tooth, the bracing element is adjusted so that the feet 133 are supported on the patient's gums astride of the tooth to provide leverage to the extraction tool.

Figure 9A:
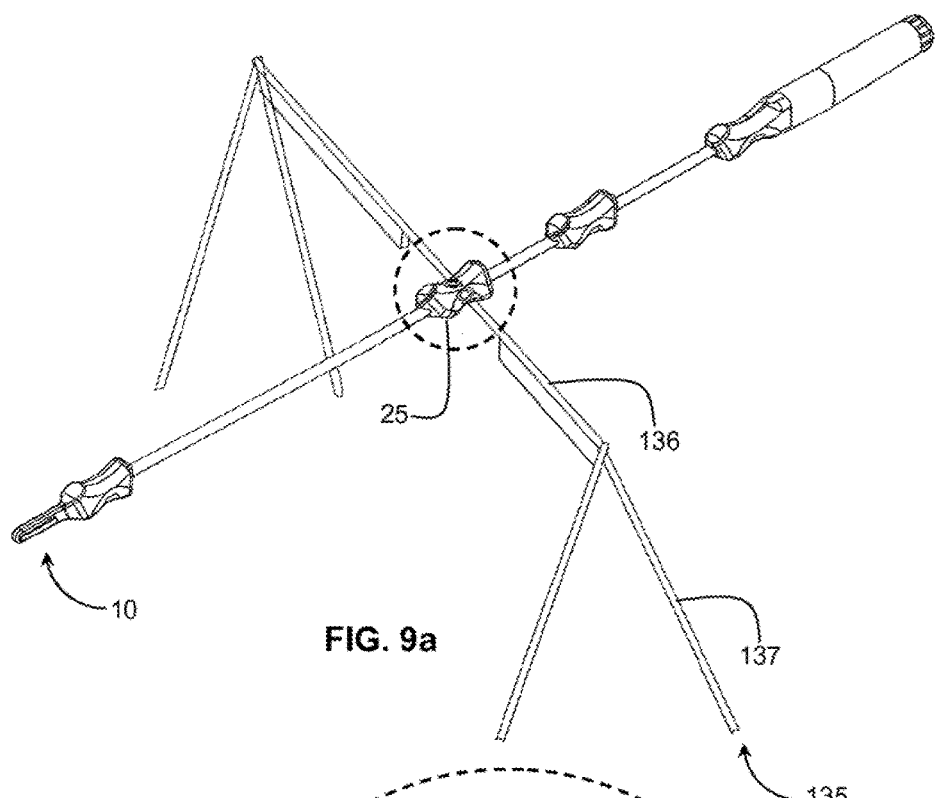
FIG. 9a shows schematically a tool rest for supporting the tool.
Figure 9B:
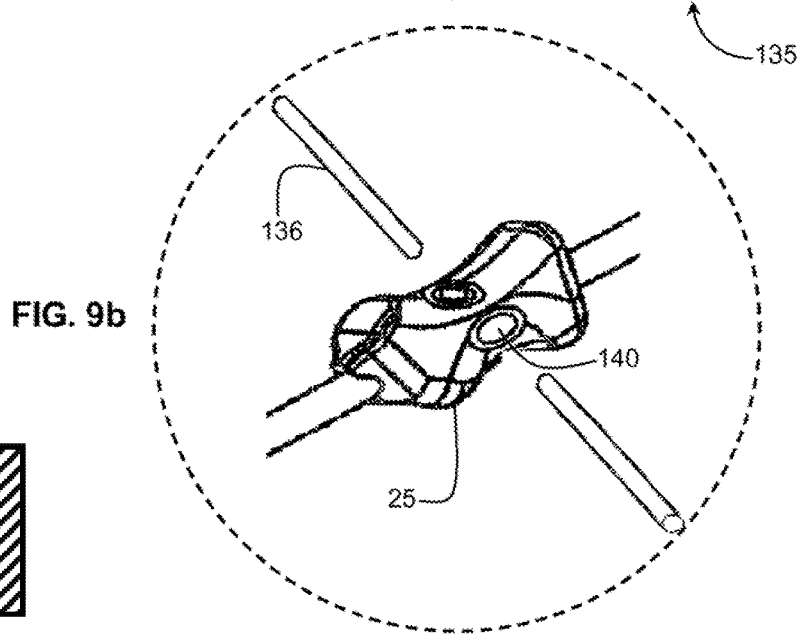
FIG. 9b shows an enlarged detail of the sleeve adapted for pivotal support by the tool rest.
Figure 9C:
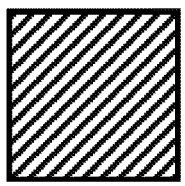
FIG. 9c shows a rod having a non-circular cross section (square in the illustration)

FIG. 9a shows schematically a tool rest 135 for supporting the instrument 10. The tool rest 135 comprises a bar 136 stably supported on a pair of legs 137 the height of which may be adjusted so as to position the bar 136 at a desired height above the working area. The legs 137 may be telescopically adjustable or angularly displaceable. The sleeve 25 of the surgical instrument 100 is supported by the bar 136, which serves as a fulcrum allowing the surgical instrument to be pivoted and manipulated during use. The sleeve 25 may simply rest on the support bar 136 or, as shown in FIG. 9b, it may have a transverse bore 140 through which the bar 136 is accommodated. As noted previously, the bar need not be uniformly circular in cross-section. In the case where the sleeve is adapted for pivotal support on the bar, the bore 140 may be part of a bearing adapted for rotation within the sleeve and having a bore of complementary shape to the bar. The bearing may be a spherical bearing allowing the tool to be rotated in both elevation and azimuth. The same effect may also be realized by allowing rotation of the bar 136 in the horizontal plane, in which case the surgical instrument may be anchored to the bar 136 so as to permit rotation of the surgical instrument in elevation but not in azimuth. In yet another embodiment the sleeve may be supported by an intermediate element supported by the bar 136. The intermediate element may be supported on a spherical bearing allowing rotation in both elevation and azimuth relative to the bar, which may then be rigidly and stably supported.

Figure 10A:
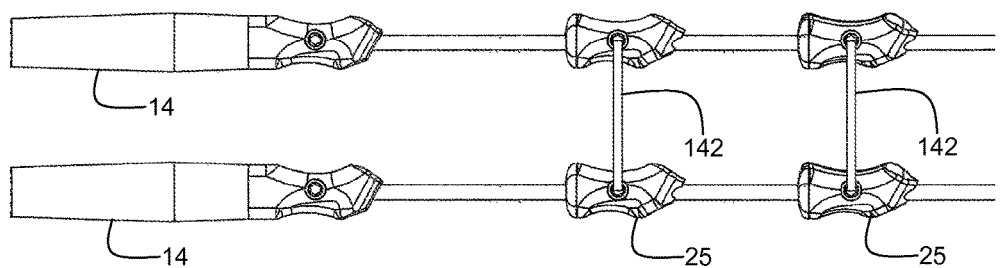
FIGS. 10a, 10b and 10c show cascaded tools according to different embodiments.
Figure 10B:
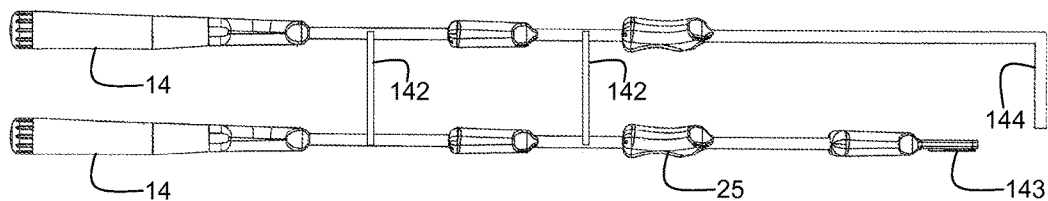
Figure 10C:
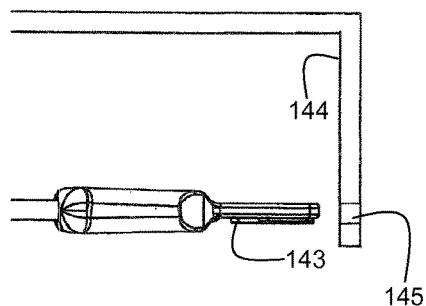
Figure 10D:
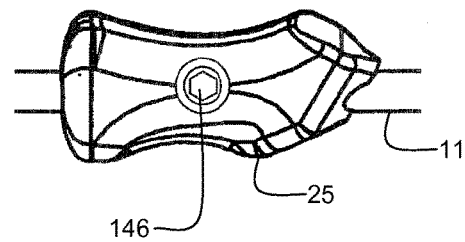
FIG. 10d shows a detail of an alternative locking member for securing the tool handle.

The tool rest 135 not only facilitates precision adjustment of the surgical instrument but it also allows two or more surgical instruments to be mounted in cascade. Such an arrangement is shown schematically in FIG. 10a where respective sleeves 25 of a pair of cascaded surgical instruments are anchored by a coupling element 142. The sleeves allow the rods of both surgical instruments to be independently rotated axially and slid forward and backward relative to the tool rest. FIG. 10b shows an alternative embodiment where the rods of the two surgical instruments are themselves anchored by a coupling element 142. One of the surgical instruments is shown as a cutting tool 143 and the other surgical instrument 144 is shown as a depth gauge or a shielding or displacement element. When used in the embodiment of FIG. 10a, it may be moved to and fro independently of the cutting tool 143 so as to allow the depth to be set. When used as a shielding element in the embodiment of FIG. 10b, the shielding element is fixed and its vertical extremity may be extended so as to overlap the line of sight of the cutting tool 143 which is capable of sliding movement relative to the shielding element. An aperture 145 in the shielding element 144 shown is aligned with the cutting tool 143 as shown in FIG. 10c to allow the cutting tool to penetrate through the aperture 145 to the skin without risk of damage to surrounding tissue. The shielding element 144 may be formed of thermally insulating material to inhibit heat flow to the surrounding tissue. FIG. 10d shows a detail of an alternative locking member in the form of a miniature hexagonal screw such as an allen screw 146 allowing the handle to be locked in position on the rod since the handles of the cascaded surgical instruments must be locked on the respective rods. The respective handles 14 of both surgical instruments in these embodiments have rotational directionality so as to allow rotation of the handles relative to the respective rods in order that their beveled grips will be optimally located by the alternate hands of the surgeon. Likewise, the working ends of both surgical instruments may be adapted for sliding movement along the rods and may be locked prior to use. Here, too, this may be achieved using self-locking collars in the mounts of the respective surgical instruments.

The invention is not limited to the details of the foregoing illustrated embodiments. The present embodiments are therefore to be considered in all respects as illustrative and not restrictive, the scope of the invention being indicated by the appended claims rather than by the foregoing description.

Thus, for example, while rotational directionality of the handle when provided may be achieved using beveled indents, it is to be understood that it may be obtained in other ways, such as employing a handle of non-uniform cross-section that favors gripping the handle in a predetermined orientation.

While the invention has been described with particular reference to a surgical scalpel, it is to be understood that the invention will find application for other surgical instruments where fine control is required.

Furthermore, all of the components of the surgical instrument may be formed of a material that allows them to be sterilized after use, so as to permit re-use of the tool. Alternatively, the tool may be disposable after use.

It should also be noted that many of the features described may be used in combination and the claims are intended to embrace all such combinations regardless of whether they are explicitly described and illustrated.

The invention claimed is:

1. A surgical instrument configured to facilitate gripping and manual adjustment by a left-handed or right-handed user, said surgical instrument comprising:
   a handle;
   a rod having first and second ends, the first end attachable to a working end of the instrument and the second end coupled to the handle which has rotational directionality for gripping by a first hand of the user,
   said handle having a grasping body with a finger reception surface recess, and said grasping body being elongated in a common direction with the direction of elongation of the rod, and said grasping body being rotatable about a rotation axis extending in the direction of elongation of the grasping body such that the grasping body rotates about the rotation axis and about the rod so as to allow the user to adjust an angular displacement of said handle relative to the working end,
   a locking member configured for preventing rotation of the handle relative to the rod after handle angular displacement adjustment to a location where the handle is comfortably located relative to the working end, and wherein said locking member, when in a locking state relative to said rod, places said handle in a state of compression and said rod in a state of axial tension, and
   a first sliding sleeve axially slideably mounted on the rod for axial slide adjustment along an exterior surface of said rod, and said first sliding sleeve being configured with a surface recess for accommodating a finger of a second hand of the user at a location between the working end and the locking member, and wherein a distal end of the first sliding sleeve is positioned proximal to a proximal end of the working end such that the working end, when in use, is exposed relative to the first sliding sleeve.

2. The surgical instrument according to claim 1, wherein: the finger recess of the handle comprises a beveled indent that extends circumferential around the grasping body periphery for accommodating adjustment of a finger of the first hand of the user about the grasping body periphery so as to facilitate said rotational directionality.

3. The surgical instrument according to claim 1, further having a second sliding sleeve, said first and second sliding sleeves being configured for gripping by alternate hands of the user, and at least one of the first and second sliding sleeves being configured for both sliding axially along the rod and holding at different positions along the rod after sliding.

4. The surgical instrument according to claim 3, wherein a first one of the first and second sliding sleeves is dimensioned for freely sliding along the rod and a second one of the first and second sliding sleeves is dimensioned for frictionally gripping the rod, while allowing it to be moved when desired.

5. A surgical instrument configured to facilitate gripping and manual adjustment by a left-handed or right-handed user, said surgical instrument comprising:
   a rod having first and second ends, the first end attachable to a working end of the instrument and the second end coupled to a handle having rotational directionality for gripping by a first hand of the user,
   the handle being rotatable about the rod so as to allow the user to adjust an angular displacement of said handle relative to the working end,
   a locking member configured for preventing rotation of the handle relative to the rod after handle angular displacement adjustment to a location where the handle is comfortably located relative to the working end, and
   a first sliding sleeve mounted on the rod and configured for accommodating a finger of a second hand of the user, and wherein a distal end of the first sliding sleeve is positioned proximal to a proximal end of the working end such that the working end, when in use, is exposed relative to the first sliding sleeve, and
   wherein the second end of the rod is screw-threaded for engaging complementary screw threads of each of the locking member and the handle, a surface of the locking member being configured in a locked position to frictionally bear against an outer surface of the handle and prevent rotation thereof, and wherein the locking member, when in a locked state, places said rod in a state of axial tension.

6. The surgical instrument according to claim 1, comprising a scalpel wherein the working end is a blade of the scalpel.

7. The surgical instrument according to claim 1, wherein the first sliding sleeve is of an axial length shorter than that of the handle, and includes a beveled indent at an intermediate location between axial ends of the first sliding sleeve.

8. The surgical instrument of claim 1 wherein the second end of the rod is configured for engaging with each of the locking member and the handle, such that, when the locking member is in a locked position, the locking member prevents relative rotation between the handle and the rod, and when in an unlocked position, there is allowed for an adjustment in rotational directionality of the handle to accommodate a left-handed or right-handed user.

9. The surgical instrument according to claim 8, further comprising a second sliding sleeve mounted on the rod intermediate first and second free ends of the rod, and said second sliding sleeve having a beveled surface for accommodating a finger of a hand of the user.

10. The surgical instrument according to claim 8, wherein the working end of the instrument comprises a beveled mount that is capable of sliding movement to allow the working end to be protracted and retracted.

11. The surgical instrument according to claim 10, wherein the mount includes a self-locking collar that slides on the end of the rod and has a quick finger release that is depressed to allowing sliding and is released to lock the mount in place.

12. The surgical instrument according to claim 10, including a locking nut to secure the mount and prevent further sliding.

13. The surgical instrument according to claim 8, wherein the second end of the rod engages with each of the locking member and the handle by way of a threaded section of the rod supported within a threaded bearing of the handle, and which threaded section of the rod is received within a threaded cap of the locking member such that rotation of the threaded cap leads to a compression locking relationship between an end surface of the handle and the threaded cap.

14. The surgical instrument according to claim 8, wherein the working end of the instrument comprises a working tool and a beveled mount that is engaged with the working tool and shaped and dimensioned to allow the working end to be gripped by a second hand of the user.

15. The surgical instrument according to claim 13 wherein the working end of the instrument has a threaded tool that is threadably engaged with a threaded section at the first end of the rod.

16. The surgical instrument according to claim 1, including an accessory mounted on the rod toward the working end.

17. The surgical instrument according to claim 16, wherein the accessory includes a mount that is fixedly or slidably mounted on the rod and supports at least one ancillary tool.

18. The surgical instrument according to claim 16, wherein the accessory includes at least one of the following:
    a tube supported within a mount for directing a fluid toward the working end or for removing a fluid therefrom;
    a digital caliper for measuring an extent of linear movement of the rod;
    a bracing element for sliding movement relative to an extraction tool constituting the working end of the surgical instrument, the bracing element being configured to provide leverage to the extraction tool during use thereof; and
    an illumination device for directing light toward the working end.

19. The surgical instrument according to claim 17, wherein the ancillary tool includes any one or more of:
    a shielding element having an aperture aligned with a cutting tool of the surgical instrument to allow the cutting tool to penetrate through the aperture without risk of damage to surrounding tissue;
    a mirror; and
    an imaging device adapted for coupling to a display device.

20. The surgical instrument according to claim 17, wherein the mount is a self-locking collar that slides on the end of the rod and has a quick finger release that is depressed to allowing sliding and is released to lock the mount in place.

21. The surgical instrument according to claim 18, including an illumination device for directing light toward the working end.

22. The surgical instrument according to claim 21, wherein the illumination device is fixed to a mount of the surgical instrument or to the mount of the accessory.

23. The surgical instrument according to claim 22, wherein:
    the illumination device is fixed to the mount of the surgical instrument, and
    the mount is rotatable on the rod, thus allowing the illumination device to be rotated independent of the accessory.

24. The surgical instrument according to claim 1, wherein the first sliding sleeve is a self-locking collar that slides on the end of the rod and has a quick finger release that is depressed to allowing sliding and is released to lock the mount in place.

25. The surgical instrument according to claim 17, wherein the ancillary tool includes a mirror or an imaging device that may be coupled to a display device so as to permit the surgeon to see a field of view.

26. The surgical instrument according to claim 1, wherein the working end is any one of: a probe, a cutting tool, a cauterizing head, a drill, a hooking element.

27. As assembly comprising two surgical instruments according to claim 1 mounted in cascade, wherein respective sleeves of said instruments are anchored by a coupling element or respective rods of the two surgical instruments are anchored by a coupling element.

28. An assembly comprising the surgical instrument of claim 1 and a support assembly that includes a support bar, and a concave portion of the sliding sleeve is in supporting contact with the support bar.

29. The surgical instrument according to claim 1, wherein the first sliding sleeve is configured as to slide axially along the exterior surface of the rod such that, in a first direction of axial slide, the first sliding sleeve slides toward the handle, and in a second direction of axial slide, the first sliding sleeve slides away from the handle, which handle remains axially fixed to the rod, and wherein, when the first sliding sleeve is at an intermediate location of slide range, an exterior surface of the rod is exposed in a region extending between the first sliding sleeve and a distal end of the handle.

* * * * *